United States Patent [19]

Lorenz et al.

[11] Patent Number: 5,420,197
[45] Date of Patent: May 30, 1995

[54] GELS FORMED BY THE INTERACTION OF POLYVINYLPYRROLIDONE WITH CHITOSAN DERIVATIVES

[75] Inventors: Donald H. Lorenz, Basking Ridge, N.J.; Connie C. Lee, New Hope, Pa.

[73] Assignee: Hydromer, Inc., Whitehouse, N.J.

[21] Appl. No.: 181,625

[22] Filed: Jan. 13, 1994

[51] Int. Cl.$^6$ .................... C08G 63/48; C08G 63/91
[52] U.S. Cl. ........................ 525/54.3; 514/55;
514/772.7; 514/777; 514/944; 523/122; 524/27;
536/20; 424/286; 424/426
[58] Field of Search ............ 525/54.3; 536/20;
524/27; 523/122; 424/486, 426; 514/55, 772.7,
777, 944

[56] References Cited

U.S. PATENT DOCUMENTS

| | | | |
|---|---|---|---|
| 4,134,412 | 1/1979 | Gross et al. | 132/7 |
| 4,202,881 | 5/1980 | Gross et al. | 424/70 |
| 4,323,557 | 4/1982 | Rosso et al. | 428/28 |
| 4,492,685 | 1/1985 | Keith et al. | 428/28 |
| 4,642,267 | 2/1987 | Creasy et al. | 428/413 |
| 4,646,730 | 3/1987 | Schonfeld et al. | 128/156 |
| 4,931,282 | 6/1990 | Asmus et al. | 424/448 |
| 4,933,182 | 6/1990 | Higashi et al. | 424/435 |
| 5,156,601 | 10/1992 | Lorenz et al. | 604/307 |
| 5,292,514 | 3/1994 | Capecchi et al. | 424/422 |
| 5,318,780 | 6/1994 | Viegas et al. | 424/427 |

FOREIGN PATENT DOCUMENTS

107376 2/1984 European Pat. Off. .

OTHER PUBLICATIONS

A. Conix and G. Smets, "Ring Opening in Lactam Polymers", J. Poly. Chem. 13, 221–229 (1955).
H. P. Frank "The Lactam–Amino Acid Equilibria for Ethylpyrrolidone and Polyvinylpyrrolidone", Journal of Polymer Science 12, 565–576 (1954).
General Aniline & Film Corporation Technical Bulletin 7583-033, "PVP".

*Primary Examiner*—Nathan M. Nutter
*Attorney, Agent, or Firm*—Hoffmann & Baron

[57] ABSTRACT

A composition includes a stable gel of neutralized chitosan and poly(N-vinyl lactam), the poly(N-vinyl lactam) having a K value of at least about 60 and mole equivalents of acid groups above about 1.4 from ring-opened pyrrolidones. The composition may also include a substrate and various additives incorporated with the gel. A method for making the gel includes mixing the chitosan and poly(N-vinyl lactam) in aqueous solution and curing. Products include wound packings, wound dressings, burn dressings, drug delivery dressings, cosmetic face masks and cosmetic wrap dressings.

32 Claims, No Drawings

GELS FORMED BY THE INTERACTION OF POLYVINYLPYRROLIDONE WITH CHITOSAN DERIVATIVES

BACKGROUND OF THE INVENTION

This invention relates to the field of poly(N-vinyl lactam)-chitosan gels and more particularly to gels which are absorbent and may be skin adhering, which are flexible and contour-conforming, and which can be used for a variety of applications.

Chitosan is a deacetylated chitin, and is a linear polysaccharide of deacetylated N-acetyl-D-glucosamine. Chitosan has been used to absorb heavy metals from water and industrial waste streams, and as a dyeing assistant in photographic emulsions. Chitosan derivatives have also been used in cosmetics and conditioning agents, in hair setting lotions and shampoos as, for example, in U.S. Pat. Nos. 4,134,412 and 4,202,881, when neutralized with acids.

Poly(N-vinyl lactam) s such as polyvinylpyrrolidone (PVP) have been used, for example, in pharmaceuticals, in certain types of films and in some cosmetic products.

It has been known that polyvinylpyrrolidone forms complexes with polyurethanes to yield hydrophilic blends or alloys. U.S. Pat. No. 4,642,267 describes hydrophilic polymer blends of polyurethane and hydrophilic poly(N-vinyl lactam) prepared in solvent solution to provide slippery coatings when wet and which are water insoluble to some extent once cured by drying.

European Patent Application 107,376 describes tacky PVP gels which require the use of ionizing radiation for cross-linking. U.S. Pat. No. 4,646,730 describes a PVP/Silver Sulfadiazine hydrogel dressing in which electron beam radiation is required to cross-link the PVP and form a gel. In addition, magnesium trisilicate, hydrogen peroxide and/or polyacrylic acid are added for color stabilization. It is apparent that there would be an advantage in making skin-adhering gels in the absence of expensive equipment and/or processing.

Ring opening of pyrrolidone groups on PVP was described by H. P. Frank, "The Lactam-Amino Acid Equilibria for Ethylpyrrolidone and Polyvinylpyrrolidone", Journal of Polymer Science 12, 565–576 (1954), and A. Conix and G. Smets, "Ring Opening in Lactam Polymers", J. Poly. Chem. 13, 221–229 (1955). The concept of ring-opened pyrrolidone groups is made use of in this invention to unexpectedly attain absorbent gels.

It is therefore an object of the invention to provide dermatologically-compatible gels having a hydrophilic absorbent property.

It is a further object to produce gels without a need for expensive equipment and/or processing.

It is another object to provide gels of poly(N-vinyl lactam) and chitosan derivatives which can be used in a variety of products such as cavity dressings, drug delivery patches, face masks and wound dressings.

SUMMARY OF THE INVENTION

Accordingly, there is provided a stable, hydrophilic gel which comprises a blend of acid-neutralized chitosan and a poly(N-vinyl lactam), with or without a plasticizer, the poly(N-vinyl lactam) having a K value of at least about 60 and mole equivalents of acid groups of at least about 1.4. The gel may be formed into a wound packing or cavity dressing where, unlike hydrocolloid dressings, it is able to absorb exudate without losing its gel structure. It can also be utilized as a drug carrier for transdermal devices and for use in dry skin masks to deliver moisturizers to the skin.

The poly(N-vinyl lactam) is preferably a polyvinylpyrrolidone having mole equivalents of acid groups of at least about 1.4 formed by ring opening of pyrrolidone groups.

The gel is prepared by mixing aqueous poly(N-vinyl lactam) solution and acid-neutralized chitosan in aqueous solution at a poly(N-vinyl lactam)/chitosan weight ratio of from about 12/1 to about 2/1, preferably from about 10/1 to about 5/1, to form a blend at about 5 wt. % to 20 wt. % total polymer concentration, preferably from about 7.5 wt. % to about 15 wt. % polymer concentration, and allowing the blend to cure until a gel is formed.

The gel preferably includes at least one additional ingredient which may be releasable from the gel. Preferably the releasable ingredient is a moisturizer, drug or other bio-effecting or body-treating material.

Preferred products for which the dressing may be used are cavity-filling wound dressings, other wound and burn dressings, drug delivery systems, and cosmetic masks and wraps.

For a better understanding of the present invention, together with other and further objects, reference is made to the following description, and its scope will be pointed out in the appended claims.

DESCRIPTION OF THE PREFERRED EMBODIMENTS

It has been found that poly(N-vinyl lactam) such as polyvinylpyrrolidone (PVP), with a degree of ring-opened pyrrolidone groups, forms hydrophilic gels with chitosans. The gels are flexible and transparent or translucent and may be used alone or with various additives. The gels can be used for wound packing, wound and burn dressings, drug delivery systems, cosmetic face and nail wraps, and other applications where the high absorption capacity of the gel and the high heat capacity and transport capacity of water as part of the hydrophilic gel can be utilized. These gels may have either a tacky quality or a non-tacky quality.

Chitosan, a natural product, is derived from chitin. Chitin is an unbranched linear polysaccharide of N-acetyl-D-glucosamine units linked by $\beta$-1,4 bonds. It is a polymer of glucose in which the hydroxyl group on C-2 is replaced by the N-acetylamino group -NHCOCH$_3$. In chitosan, the acetyl group is absent. Therefore, chitosan is a deacetylated chitin. Chitosan contains approximately 7% nitrogen and is structurally similar to cellulose. Chitin occurs in nature in the exoskeletons of arthropods such as crabs, lobsters and shrimp. Chitin can be obtained from these sources as an amorphous powder after dissolution of the calcium carbonate with mineral acids and removal of the proteins. It is also found in some fungi, algae and yeasts.

Chitosan becomes soluble in water when protonated with acids. The polymer thus formed is positively charged and thus more likely to interact with negatively charged surfaces like skin and hair.

Chitosan derivatives are commercially available as, for example, chitosan neutralized with pyrrolidone carboxylic acid available as Kytamer PCA from Amerchol Corporation; carboxymethyl sodium salt of chitosan available as Chitisol from Muto Corporation; chitosan neutralized with glutamic acid available as Seacure+210 from Protan Corporation; N,O-carboxymethyl chitosan available from Nova Chem Ltd., Canada; and un-neutralized chitosan available from Tokyo Kasei Inc. Suitable chitosan derivatives for this invention are the dermatologically-compatible salts of chitosan such as those with pyrrolidone carboxylic acid, glutamic acid, acetate, etc., and also N,O-carboxymethyl chitosan.

Suitable poly(N-vinyl lactams) have a K value of at least about 60, preferably at least about 70, and most preferably from about 80 to about 110. The K value represents a function of molecular weight. The K value is derived from viscosity measurements and is calculated according to Eikentscher's formula described by Kline, G. M., "Polyvinylpyrrolidone", Modern Plastics p 157 (Nov. 1945) and is also described in General Aniline & Film Corporation Technical Bulletin 7583-033. At the same K value or molecular weight, the level of ring-opened poly(N-vinyl lactam) is an important consideration in determining whether a gel forms.

In the invention, poly N-vinyl lactams containing above certain levels of ring-opened pyrrolidone groups, when mixed with certain solutions of neutralized chitosans, form gels which may be mildly tacky. The term tacky is intended to mean having the property of being sticky to the touch or adhesive to a degree that the gel is capable of sticking to the skin while being easily removable when removal is desired.

The term poly(N-vinyl lactam) as used herein shall be understood to include homopolymers, copolymers and terpolymers of N-vinyl lactams such as N-vinylpyrrolidone, N-vinylbutyrolactam, N-vinylcaprolactam, and the like, as well as the foregoing prepared with minor amounts, for example, up to about 20 weight percent, of one or a mixture of other vinyl monomers copolymerizable with the N-vinyl lactams. Copolymers or terpolymers of poly(N-vinyl-lactam) may comprise N-vinyllactam monomers such as vinylpyrrolidone copolymerized with monomers containing a vinyl functional group such as acrylates, hydroxyalkylacrylates, methacrylates, acrylic acid or methacrylic acid, and acrylamides. Of the poly(N-vinyl lactam) homopolymers, the polyvinylpyrrolidone (PVP) homopolymers are preferred. Of the poly(N-vinyl lactam) copolymers, vinyl pyrrolidone, acrylamide copolymers are preferred. A suitable poly(N-vinyl lactam) terpolymer is vinylpyrrolidone, vinylcaprolactam, dimethylaminoethyl methacrylate. A variety of polyvinylpyrrolidones are commercially available. It is important, however, for the poly(N-vinyl lactam) to contain a degree of ring-opened lactam groups.

A lactam may be considered to be a cyclic amide produced from an amino acid through the elimination of a molecule of water from the —COOH and —NH$_2$ groups. A lactam, therefore, contains a —NH—CO— group in a ring. An N-vinyl lactam has a vinyl group at the ring nitrogen and the monomer can be polymerized through the vinyl group. In a ring-opened poly(N-vinyl lactam), the vinyl backbone may be considered to remain essentially intact, but some lactam rings are opened to make available —COOH groups. The availability of these —COOH groups may be measured through base titration to determine the mole equivalents of base per mole of acid groups in a specific poly(N-vinyl lactam). Because the polymer backbone remains essentially intact, different poly(N-vinyl lactams) having the same molecular weight or K value may have different levels of ring openings. The poly(N-vinyl lactams) useful in forming the gels in the invention have a mole equivalent/mole of acid groups greater than about 1.4, preferably greater than about 2.0. In the absence of opened lactam rings, the gel does not form. The poly(N-vinyl lactams) are preferably of relatively high molecular weight as indicated by a K value above about 60.

Ring opening in poly(N-vinyl lactams) may be effected by heating a solution of the poly(N-vinyl lactam) at a temperature of from about 50° C. to about 120° C., with from about 60° C. to about 100° C. preferred, at pressure from about 15 psi to about 150 psi for from about one half hour to about 10 days, with from about one hour to about 24 hours preferred. The solvent for the solution is preferably aqueous and may include a small amount of a weak base such as dilute ammonium hydroxide or dilute sodium hydroxide to result in a solution which is slightly basic, e.g. having a pH of about 7–9, with about 7–8 or 7–8.5 preferred. If time saving is an important consideration as in commercial operations, ring opening may be carried out, for example, for shorter periods of time in a reactor under conditions of high temperature and pressure, e.g. 200° C. at 50 psi.

To form the gel, the poly(N-vinyl lactam) is mixed or blended with neutralized chitosan. At certain ratios of PVP/chitosan derivatives, a mixture of these two components forms a highly water-swellable gel within a short time of mixing.

The gel may be prepared by dissolving the poly(N-vinyl lactam) such as polyvinylpyrrolidone in aqueous solution, then adding an aqueous solution of neutralized chitosan with sufficient agitation to attain a homogenous mixture. The solvent used for the gel preparation is preferably substantially aqueous. For example, the gels may be prepared in water or in hydroalcohols such as water/isopropyl alcohol and water/ethanol. The gels form at a ratio of PVP/chitosan of from about 12/1 to about 2/1, preferably from about 10/1 to about 5/1. At higher PVP to chitosan ratios gels are formed but may lead to a sticky residue and may contain uncomplexed PVP which will leach out in water. The total polymer concentration as well as the ratios of the two polymer components at which the gel is made shows an effect on the consistency of the gel, which becomes softer at lower concentrations. Decreasing the total polymer concentration also leads to softer gels at a given PVP-chitosan ratio. The gels may be made with a total polymer content ranging from about 5 to about 20 wt. %, preferably from about 7.5 wt. % to about 15 wt. % solids. At lower solids levels or when the PVP has a K below about 80, gels may form but they are not as consistent. The blend may be allowed to cure for a time of from a few seconds to about 20 minutes. The time and temperature for curing are not critical. For purposes of convenience, ambient temperature may be used but the time can be shortened at elevated temperatures. The term gel is intended to mean viscous or semi-solid and jelly-like.

The preferred gels are stable and therefore maintain their physical integrity after absorbing large quantities of liquid. The gels can be sterilized by radiation sterilization. The gels are hydrophilic and capable of absorbing many times their weight in water or at least twice their weight in water. For practical application as described herein, a gel absorbs, for example, from about 4 to 10 times its dry weight in water or saline solution (0.9% NaCl), depending on the ratio of PVP/chitosan. For example, at a ratio of PVP/chitosan of about 2/1, the gel absorbs about 4 times its dry weight (i.e. solids weight) in saline solution; at a ratio of 10/1, it can absorb about 10 times its dry weight in saline solution.

While the exact nature of the mechanism by which the gel forms is not known, and while it is not intended to be bound by theory, it is believed to be caused by pervasive and tight hydrogen bonds between chains. The presence of the ring-opened pyrrolidones, in some undetermined way, plays an imperative role in achieving this goal.

Wetting, dispersing agents or surfactants as are known in the art, such as block copolymers of ethylene oxide and propylene oxide, may be added to the blends in an amount of from about 1 to about 5 weight percent, preferably from about 1 to about 3 weight percent, to reduce adherence to the skin.

Glycerine in an amount of from about 5 to about 50 weight percent, preferably from about 10 to about 30 weight percent may be added to the gel preparation to increase tack and pliability after drying. The glycerine is preferably mixed into the PVP solution prior to adding neutralized chitosan solution. Propylene glycol or low molecular weight polyethylene glycol may also be used.

Many different types of additional materials may be incorporated into the gels including organic salts, inorganic salts at low levels, alcohols, amines, polymer lattices, fillers, surfactants, pigments, dyes, fragrances and so forth as long as they do not interfere with gel formation. Many of these materials can be released from the gel.

The gels of this invention are especially useful as carriers for a wide variety of releasable biologically-active substances having curative or therapeutic value for human or non-human animals. Included among the biologically-active materials which are suitable for incorporation into the gels of the invention are hypnotics, sedatives, tranquilizers, anti-convulsants, muscle relaxants, analgesics, antipyretic agents, anti-inflammatory agents, local anesthetics, antispasmodics, antiulcer agents, antivirals, antibacterials, antifungals, sympathomimetic agents, cardiovascular agents, antitumor agents, and so forth. A biologically-active substance is added in pharmaceutically-active amounts.

Particularly preferred as biologically-active additives are nitroglycerine, scopolamine, pilocarpine, ergotamine tartrate, phenylpropanolamine, and theophylline; also antimicrobials tetracycline, neomycin, oxytetracycline, triclosan, sodium cefazolin, silver sulfadiazine, and also salicylates such as methylsalicylate and salicylic acid, nicotinates such as methyl nicotinate, capsicum and benzocaine. When the gel is to be used, for example, for cosmetic treatment, hydrating agents such as sodium pyrrolidine carboxylic acid may be added. For a hydrating purpose, however, the large amount of water alone which can be absorbed by the hydrophilic gel serves a hydrating function to the skin.

Water-soluble and water-insoluble additives such as those described above may be initially mixed with the aqueous solvent before the gel preparation is begun, may be mixed with the aqueous solution of poly(N-vinyl lactam) or mixed with the aqueous solution of neutralized chitosan during the gel preparation. Water-soluble ingredients are preferably mixed in with the PVP prior to admixing with chitosan. Many water-insoluble ingredients can be mixed with chitosan prior to adding to PVP. One can also emulsify water insolubles by adding surfactants to either the PVP or chitosan. Alternatively, additives may be similarly mixed into the gel preparation after the poly(N-vinyl lactam) is blended with the chitosan. Additives may also be applied to the surface of a gel dressing, for example, by spraying, dipping, brushing or rolling.

The gel may be used to make adsorbent wound packing agents or dressings, skin masks or wraps, drug delivery patches and dry film products.

When the gel is used as a wound packing or cavity-filling wound dressing, it advantageously provides the desired properties of such dressings, such as (1) biocompatability; (2) ability to conform to a wound cavity; (3) non-adherence to the wound; (4) absorbs exudate; (5) removable in one piece from the wound; (6) holds its physical integrity when swollen with exudate; (7) is not too sticky for handling.

When used as a skin-hydrating mask, the gel has excellent hydrating capacity, advantageously contains no alcohol, and is easily and cleanly removed.

When made into a dry film and used as a skin mask, it provides a flexible, clear, hydrophilic film which adheres to the skin when wetted with water. The film can retain active moisturizers and other ingredients close to the skin, helping in their delivery. The film can also be easily peeled off after a period of time without leaving residues.

To obtain the products of the invention, the gel may be packaged by itself in a mold, in a dry film form, or as a two-part system which requires mixing prior to use; or may be provided on a substrate and covered with a release liner to prevent the gel from sticking to itself. The release liner is removed prior to application to skin. The substrate may fulfill one or several functions including providing reinforcement, providing a gas and liquid barrier, providing a support with air permeability, providing protection for the gel and the area of treatment, etc. Substrate selection to provide the desired properties is known to those skilled in the art.

The gel may be coated or spread onto a backing or substrate by any means known in the art. The gel can be combined with and adhered to a virtually unlimited variety of substrates or backings including resins, metal foils, woven and non-woven webs of natural and synthetic fibers, etc. A backing which provides gas and liquid barrier properties may be a polymer film such as polyurethane. Desirable composites with the gel may also be made using films of polyester, polyvinyl alcohol, or polyvinylidene chloride. When the gel has a barrier substrate, the resulting structure has particular utility as a wound and burn dressing. Moisture is kept in and excess exudate is absorbed to promote healing but bacteria are prevented from entering the wound or burn area, and microbial stasis may be maintained through the incorporation of an anti-microbial agent into the gel to prevent infection. For ease of use, the tacky gel on a backing is covered with a release liner which may be a silicone-coated film or polyethylene.

The gel may be coated onto the backing so that the gel occupies all or part of the backing surface. If the gel occupies part of the backing surface, non-gel coated areas of the backing may be provided with an additional adhesive. A dressing of this type is positioned on the skin so that the additional skin adhesive comes into contact with intact skin while the absorbent gel contacts a wound. The additional adhesive provides a dressing with staying power when the absorbent gel has become substantially saturated with wound exudate thus losing some of its adhesiveness through a dilution effect.

In still another embodiment, the gel may be used in cosmetic preparations such as face masks and nail wraps. The gel serves a hydrating function with or without a backing and a cosmetic effect may be enhanced with the incorporation of other ingredients. A kit for a cosmetic gel may comprise a ready-made gel or two components: a poly(N-vinyl lactam) component and a chitosan component. Other cosmetic agents such as hydrating agents, fragrances, etc. can also be supplied to the ready-made gel or to either component. For use, the components may be mixed and applied. The gel advantageously can be easily peeled off after use. It shall be understood that the term cosmetic means a preparation intended to enhance or improve physical appearance.

In a further embodiment, fragrances may be incorporated into the gel. When the gel is kept moist in a suitable vented container, the fragrance is slowly released as an air freshener.

The following examples are intended to illustrate but not limit the invention.

EXAMPLE 1

A PVP with a K value of 92 was titrated with base. The results showed that the PVP had 1.4 mole equivalents/mole of acid groups. Attempts to form a gel with chitosan using this PVP were unsuccessful.

EXAMPLE 2

The PVP of Example 1 was heated in water at 60° C. for eight days, then at 95° C. for eight hours. This material, when titrated with base, showed 2.15 mole equivalents/mole of acid groups and formed a highly swellable gel at a weight ratio of 10 PVP/1 chitosan at 10% total polymer concentration.

EXAMPLE 3

A PVP (Luviskol-brand, BASF Corporation) having a K value of 93 was titrated with base and showed less than 1 mole equivalent/mole of acid groups. Attempts to form a gel using this PVP with chitosan were unsuccessful.

EXAMPLE 4

A commercial PVP (Kollidon 90, BASF Corporation), having a K value of 93 was titrated with base and showed 5 mole equivalents/mole of acid groups. When mixed with chitosan, this PVP forms a hydrophilic gel.

EXAMPLE 5

To 8.6 grams of a 25% water solution of PVP described in Example 4 was added 1.4 grams propylene glycol and 3.0 grams of a 20% aqueous solution of a block copolymer of ethylene oxide and propylene oxide (Pluronic F88, BASF Corporation). To that solution was added 5 grams of a 3% aqueous solution of chitosan neutralized with pyrrolidone carboxylic acid (Kytamer PCA, Amerchol Corporation). The mixture was stirred for one minute then applied to wet human skin. It quickly became non-flowable and could be rolled or peeled from the skin.

The gel, when put into excess water or saline solution at room temperature, absorbed additional liquid but did not dissolve or disintegrate.

EXAMPLE 6

5.0 grams of a 20% solution of PVP in water containing at least 2 mole equivalents/mole of acid containing groups were mixed with 5.0 grams of a 2% solution of N,O-carboxymethyl chitosan (NOCC, Nova Chem Ltd.). The mixture was poured into a hemispherical mold. It set in 10 seconds at room temperature to a mildly tacky, non-flowable gel. The gel was pliable and relatively non-adherent to a wound.

The gel, when put into excess water or saline solution at room temperature, absorbed water but did not dissolve or disintegrate.

EXAMPLE 7

A solution of 5.0 g of 20% PVP containing more than 2 mole equivalents/mole of acid groups, 5 grams of deionized water, 5.0 g of 2% neutralized chitosan, 0.25 grams of polyethylene glycol (carbowax 400, Union Carbide Corporation) as a plasticizer and 0.25 grams of a block copolymer of ethylene glycol and propylene glycol (Pluronic F88, BASF Corporation) for easier release from a substrate were mixed and coated in a thickness of 1 mm on a polyester film substrate.

The coating was dried in an oven to form a 0.05 mm thick dried film that can be die cut to specific shapes, e.g., for moisturizing face masks or eye patches. Before the film is applied to skin, the skin is sprayed or wetted with water.

EXAMPLE 8

The dried film of Example 7 was soaked in water and 0.9% sodium chloride solution at room temperature. In both liquid media, the film absorbed large amounts of liquids, expanding in the process.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A dermatologically-compatible composition comprising a hydrophilic gel which comprises a blend of a neutralized chitosan and a hydrophilic poly(N-vinyl lactam) having a K value of at least 60 and above 1.4 mole equivalents of available acid groups.

2. The composition of claim 1 wherein the poly(N-vinyl lactam) comprises polyvinylpyrrolidone homopolymer, copolymer or terpolymer.

3. The composition of claim 1 wherein the gel comprises a poly(N-vinyl lactam)/chitosan weight ratio of from about 12/1 to about 2/1.

4. The composition of claim 1 wherein the gel is prepared in an aqueous solution at a total polymer concentration of from about 5 weight percent to about 20 weight percent poly(N-vinyl lactam) and chitosan.

5. The composition of claim 4 wherein the solution comprises water or a mixture of water and alcohol.

6. The composition of claim 1 wherein the poly(N-vinyl lactam) has mole equivalents of available acid groups of at least 2.0.

7. The composition of claim 1 which further comprises at least one substrate.

8. The composition of claim 7 wherein the substrate is selected from a group consisting of polymer film, collagen film, woven fabric, and non-woven fabric.

9. The composition of claim 7 wherein the substrate is a polyurethane film.

10. The composition of claim 7 wherein the substrate is a polyester film.

11. The composition of claim 7 wherein the substrate is stretchable.

12. The composition of claim 7 wherein the substrate is a release liner.

13. The composition of claim 1 wherein the gel comprises at least one additional ingredient.

14. The composition of claim 13 wherein the additional ingredient is a surfactant.

15. The composition of claim 13 wherein the additional ingredient is releasable from the gel.

16. The composition of claim 15 wherein the additional ingredient is a fragrance.

17. The composition of claim 15 wherein the additional ingredient is a biologically-active material.

18. The composition of claim 17 wherein the additional ingredient is selected from a group consisting of nitroglycerine, scopolamine, pilocarpine, ergotamine tartrate, phenylpropanolamine, theophylline, tetracycline, neomycin, oxytetracycline, triclosan, sodium cefazolin, silver sulfadiazine, salicylates, nicotinates, capsaicin and benzocaine.

19. A method for preparing a stable, mildly tacky, hydrophilic gel comprising mixing an aqueous dissolved poly(N-vinyl lactam) homopolymer or copolymer having a K value of at least 60 and above 1.4 mole equivalents of available acid groups and an aqueous solution of neutralized chitosan in a poly(N-vinyl lactam)/chitosan ratio of from about 12/1 to about 2/1, with a total polymer content above 5 weight percent to produce a blend, and allowing the blend to cure for a time of about 10 seconds to about 2 hours until a gel is formed.

20. The method of claim 19 which further comprises treating a poly(N-vinyl lactam) to increase mole equivalents of acid groups to above 1.4 by heating the poly(N-vinyl lactam) in aqueous solution at a temperature of from about 50° C. to about 200° C., at a pressure of from about 15 psi to about 150 psi, for about one-half hour to about 10 days.

21. The method of claim 20 wherein the aqueous solution has a pH of from about 4 to about 8.

22. The method of claim 19 which further comprises adding a biologically-active material to the blend.

23. The method of claim 22 wherein the biologically-active material is an antimicrobial agent.

24. The method of claim 19 wherein the blend is formed into a dressing by coating or casting the blend onto a substrate.

25. The method of claim 24 wherein the blend is covered with a second substrate which is a release liner.

26. The method of claim 19 wherein the blend is formed into a dressing by casting two separate slabs of gel onto two separate substrates, applying a solution of a biologically-active material to a surface of one of the slabs, and compressing the slabs together so that the biologically active material is located between the slabs.

27. The method of claim 26 wherein the biologically-active material is selected from the group consisting of salicylates, nicotinates and capsaicin.

28. The composition of claim 1 in the form of a product selected from a group consisting of wound packings, wound dressings, burn dressings, drug delivery dressings, dry films, cosmetic mask dressings and cosmetic wrap dressings.

29. The composition of claim 28 in the form of a wound packing or cavity dressing without a substrate.

30. The composition of claim 1 in the form of a dry film.

31. A stable, hydrophilic gel which comprises a blend of neutralized chitosan and a hydrophilic poly(N-vinyl lactam) having a K value of at least 60 and above 1.4 mole equivalents of available acid groups, the chitosan and poly(N-vinyl lactam) combined in a chitosan/poly(N-vinyl lactam) weight ratio from about 12/1 to about 2/1 in an aqueous solution at a total polymer concentration of at least five weight percent.

32. The composition of claim 1 wherein the neutralized chitosan includes a member of the group consisting of pyrrolidone carboxylic acid, glutamic acid, acetate and carboxymethyl.

* * * * *